United States Patent [19]

Larson

[11] 4,097,607
[45] Jun. 27, 1978

[54] DETERRENT COMPOSITION, METHOD OF USING SAME, AND ARTICLE COATED THEREBY

[76] Inventor: Kenneth A. Larson, 225 Commerce Dr., Fort Collins, Colo. 80522

[21] Appl. No.: 749,303

[22] Filed: Dec. 10, 1976

[51] Int. Cl.$^2$ .................... A61K 31/11; A61K 31/165
[52] U.S. Cl. .................................... 424/324; 252/365; 424/333
[58] Field of Search ................. 252/365; 424/324, 333

[56] References Cited

U.S. PATENT DOCUMENTS

| 3,457,314 | 7/1969 | Siedel et al. | 424/333 |
| 3,848,060 | 11/1974 | Izana et al. | 424/333 |
| 4,065,576 | 12/1977 | Oita et al. | 424/333 |

OTHER PUBLICATIONS

Lehner et al., Chemical Abstracts, vol. 84, No. 25, Jun. 21, 1976, p. 172, Abstract No. 175119g.

The Condensed Chemical Dictionary, 8th Ed., Van Nostrand Reinhold Co., N.Y., 1971, p. 165.
The Encyclopedia Americana, Americana Corp., N.Y., 1964, vol. 3, p. 573.
The Merck Index, 8th ed., Merck and Co., Inc., Rahway, N.J., 1968, p. 203.

*Primary Examiner*—Benjamin R. Padgett
*Assistant Examiner*—Christine M. Nucker
*Attorney, Agent, or Firm*—Eric P. Schellin

[57] ABSTRACT

An animal deterrent composition comprises cinnamic aldehyde as the active ingredient in a diluent vehicle. Capsaicin may be included as an additional active ingredient.

The composition is applied to various objects to deter attack or close approach by animals. Examples of the objects are wooden animal stalls, so as to prevent "cribbing," bandages and plaster casts on animals to deter chewing thereof and sheep collars or sheep's wool, so as to repel predators, or in farm sheds to repel porcupines.

15 Claims, No Drawings

DETERRENT COMPOSITION, METHOD OF USING SAME, AND ARTICLE COATED THEREBY

BRIEF SUMMARY OF INVENTION

In order to control the behavior of animals or predators, use has been made of various deterrents. These are substances which emit an odor or have a taste which is disagreeable and repellant to the animal, so that the animal tries to avoid the substance.

For example: Some horses and dogs, when kept in wooden stalls and kennels, chew the wood, a practice known as "cribbing." A deterrent applied to the wood reduces or eliminates the chewing.

Domestic animals frequently chew plaster casts or bandages placed on their bodies, and it is useful if the cast or bandage is protected with a deterrent.

A very small minority of coyotes prey on live sheep and are not reached by the predator control programs because they avoid dead sheep, such as carcasses which have been poisoned. This very small minority of coyotes can be controlled for limited periods of time by coating at least some of the sheep in the flock with a deterrent. Before the rare killer coyote becomes familiar with the odor of the repellant, the flock may have been removed.

Porcupines are well known as nuisances around farm sheds and recreational camps, and it is desirable to use repellants to curb the damage they cause.

Pigeons and starlings can also be nuisances, and attempts have been made to use deterrents to control them.

In the past, various substances such as coal tars have been used as deterrents. Many of the previously used deterrents are poisonous and this obviously has some disadvantage, where the animal to be controlled is of value.

Applicant has discovered that cinnamic aldehyde (also known as cinnamaldehyde, 3-phenylpropenal and cinnamyl aldehyde) having the formula $C_6H_5CH:CHCHO$, is generally repellant to many domesticated and predatory animals. This is rather surprising, since cinnamic aldehyde is the active ingredient in the spice cinnamon and is generally not repellant to humans, but instead is used for its pleasure giving flavor in many foods and is also widely used for its pleasure giving fragrance.

Applicant has also discovered that capsaicin, an alkaloid, having the formula $C_{18}H_{27}O_3N$, in combination with cinnamic aldehyde, is useful in a composition which is generally repellant to the above-mentioned animals. Capsaicin is a principal active ingredient of the spice cayenne pepper.

Both cinnamic aldehyde and capsaicin are substantially insoluble in water but dissolve in ethyl alcohol. An alcoholic solution of these deterrents is a convenient composition for applying a deterrent coating to various objects, such as an animal stall, or a bandage or cast on the animal, or a collar on the animal.

The solution can be applied, for example, from a user's container having a dispensing swab mounted inside the container cap, or it can be hand-sprayed, power-sprayed, brushed or rolled. When the alcohol has evaporated, the residue of cinnamic aldehyde and capsaicin is not easily removed by rain because it is substantially water insoluble.

The cinnamic aldehyde and capsaicin can also be applied in paste form. The paste is, for outdoor use, preferably a water resistant type, so that it is not washed off by rain. The paste may be dispensed either in open-top jars or in collapsible metal roll-up tubes. The latter is especially convenient for topical application of small amounts of paste to small areas.

It is to be noted that one of the advantages of the instant invention is that the environment is not harmed by poisonous, long-lasting residues. The active ingredients, far from being poisonous, are actually harmless and are common ingredients of human food.

The deterrent is generally applied directly to the object to be protected or to an object in the immediate vicinity. Sheep can be protected from the rare killer coyotes either by applying the deterrent to the wool in the region behind the head and upper neck, or to collars which are worn by the sheep.

DETAILED DESCRIPTION

The invention can be carried out in various ways, of which the following are exemplary:

EXAMPLE 1

Cinnamic aldehyde: 10 parts
Ethyl alcohol, denatured, 70%: 90 parts

The above solution is approximately half saturated. Accordingly, this solution, when dispensed in a one pound container with a screw cap brush applicator, can repeatedly and readily be applied to surfaces, as desired, without sufficient loss of alcohol by evaporation from the mixture still remaining in the bottle to produce a precipitate of the active ingredient. This composition can also be sprayed, either by hand or by power, or brushed or rolled on to surfaces.

EXAMPLE 2

Cinnamic aldehyde: 10 parts
Capsaicin: 5 parts
Ethyl alcohol, denatured, 70%: 85 parts The composition of this example is similar in its properties and use to that of Example 1, but its deterrent effects are somewhat more extended, due to the inclusion of the capsaicin.

In Examples 1 and 2 the ethyl alcohol is a fugitive ingredient which is not present in the final deterrent coating. Accordingly, any other suitable solvent can be substituted. However, denatured ethyl alcohol is designated as the solvent in these examples because it is economical and its fumes are of low toxicity.

Instead of using a suitable solvent, a water base diluent using a dispersing agent to suspend or emulsify the active ingredient may be used.

EXAMPLE 3

Cinnamic aldehyde: 10 parts
Capsaicin: 5 parts
Yellow beeswax: 8 parts
Benzoinated lard: 77 parts This example is a modification of the Strong Capsaicum Ointment of the British Pharaceutical Codex, 1934. It has a soft texture adapted to be squeezed out of a collapsible metal tube. The ointment is not readily removed by rain.

EXAMPLE 4

Cinnamic aldehyde: 10 parts
Capsaicin: 5 parts

Yellow wax: 4 parts
Petrolatum: 81 parts

This example is a modification of the Yellow Ointment, a standard ointment base, of the National Formularly XIII. The ointment is not readily removed by rain.

EXAMPLES 5 AND 6

These examples are identical to Examples 3 and 4, respectively, but with the capsaicin ingredient omitted.

In the examples given above, the active ingredient is stated to be cinnamic aldehyde and capsaicin. It is to be understood that each of these are the purified form of an active ingredient and that a proportionate amount of a less purified active ingredient can be substituted. Thus, it is obviously not necessary to utilize a laboratory grade of active ingredient to practice the invention, and a much cheaper commercial grade, not permissible for other uses, as in foodstuffs, is acceptable. Indeed, capsaicin is seldom sold as such in commerce, but is conventionally obtained in its impure form, capsicin, also known as capsicum oleoresin.

It is known in the prior art to use a bitter agent as a deterrent. It is to be understood that a composition in accordance with the invention may also include a bitter agent, if desired, thereby providing a modified composition having modified deterrent properties, characteristic of the invention and of the prior art as well.

I claim:

1. A deterrent for mammals comprising a carrier and an effective amount of cinnamic aldehyde wherein the carrier is an ointment which is substantially insoluble in water.

2. The composition of claim 1 including an effective amount of capsaicin.

3. A deterrent for mammals comprising a carrier and effective amounts of cinnamic aldehyde and capsaicin.

4. The composition of claim 3 where in the carrier is etheyl alcohol.

5. A method for repelling a mammal from a locus comprising applying to said locus a carrier and an effective amount of cinnamic aldehyde.

6. The method of claim 5 wherein the carrier is ethyl alcohol.

7. The method of claim 5 wherein the carrier is an ointment which is substantially insoluble in water.

8. A method for repelling a mammal from a locus comprising applying to said locus a carrier and effective amounts of cinnamic aldehyde and capsaicin.

9. The method of claim 8 wherein the carrier is ethyl alcohol.

10. The method of claim 8 wherein the carrier is an ointment which is substantially insoluble in water.

11. The method of claim 5 wherein the locus is a wooden object.

12. The method of claim 5 wherein the locus is a bandage.

13. The method of claim 5 wherein the locus is a plaster cast.

14. The method of claim 5 wherein the locus is the skin of a living domestic animal.

15. The method of claim 5 wherein the locus is an animal collar.

* * * * *